United States Patent
Kuiken

(10) Patent No.: US 9,615,864 B2
(45) Date of Patent: Apr. 11, 2017

(54) LIMB LENGTHENING SYSTEM FOR RESIDUAL LIMB

(71) Applicant: Rehabilitation Institute of Chicago, Chicago, IL (US)

(72) Inventor: Todd Kuiken, Chicago, IL (US)

(73) Assignee: Rehabilitation Institute of Chicago, Chicago, IL (US)

( * ) Notice: Subject to any disclaimer, the term of this patent is extended or adjusted under 35 U.S.C. 154(b) by 293 days.

(21) Appl. No.: 13/907,630

(22) Filed: May 31, 2013

(65) Prior Publication Data

US 2014/0358144 A1    Dec. 4, 2014

(51) Int. Cl.
  *A61B 17/72* (2006.01)
  *A61B 17/17* (2006.01)
  *A61B 17/66* (2006.01)

(52) U.S. Cl.
  CPC ...... *A61B 17/7216* (2013.01); *A61B 17/1725* (2013.01); *A61B 17/66* (2013.01); *A61B 17/72* (2013.01)

(58) Field of Classification Search
  CPC ...................................... A61B 17/72–17/7291
  USPC ...................................................... 606/62–68
  See application file for complete search history.

(56) References Cited

U.S. PATENT DOCUMENTS

| 4,384,373 | A |   | 5/1983  | Sivash |           |
|-----------|---|---|---------|-----------|-----------|
| 4,502,160 | A |   | 3/1985  | Moore     |           |
| 4,892,546 | A |   | 1/1990  | Kotz et al. |         |
| 5,108,452 | A | * | 4/1992  | Fallin    | 623/22.42 |
| 5,466,261 | A | * | 11/1995 | Richelsoph | 623/23.47 |

(Continued)

FOREIGN PATENT DOCUMENTS

| DE | 20012536 | 1/2001 |
|----|----------|--------|
| EP | 2151208  | 2/2010 |

(Continued)

OTHER PUBLICATIONS

Cole, J. Dean, M.D., Intramedullary Skeletal Kinetic Distractor, Tibial Surgical Technique, Orthofix, Nov. 2005. 28 pages.

(Continued)

*Primary Examiner* — Nicholas Plionis
(74) *Attorney, Agent, or Firm* — Polsinelli PC; Ari M. Bai

(57) ABSTRACT

An Intramedullary Distraction Osteotomy (IM DO) apparatus and corresponding methods are disclosed that allow for the patient or another to lengthen residual bone. The apparatus may be inserted into the intramedullary canal of the residual bone and may be lengthened through the application of a traction force. The apparatus protrudes from the body through a single percutaneous site. Lengthening of the amputated limb is achieved by the application of a controlled traction force that is generated by turning a lengthening knob external to the percutaneous site. One or more additional screw segments may be utilized to assist in limb lengthening. The traction force serves to separate a distal bone segment from a proximal bone segment at a specified, controllable rate, allowing new bone growth to fill in the resulting gap. Components of the apparatus provide support and alignment to the residual bone during both the lengthening and consolidation phases. External components of the apparatus may be removed after desired limb length has been achieved, reducing the risk of infection and improving patient mobility.

22 Claims, 3 Drawing Sheets

(56) References Cited

U.S. PATENT DOCUMENTS

| | | | |
|---|---|---|---|
| 5,505,733 | A | 4/1996 | Justin et al. |
| 5,516,335 | A | 5/1996 | Kummer et al. |
| 6,280,191 | B1 | 8/2001 | Gordon |
| 6,293,947 | B1 | 9/2001 | Buchbinder |
| 6,383,165 | B1 | 5/2002 | Maget et al. |
| 6,755,862 | B2 | 6/2004 | Keynan |
| 7,476,228 | B2 | 1/2009 | Abdou |
| 7,530,981 | B2 | 5/2009 | Kutsenko |
| 7,615,036 | B2 | 11/2009 | Joshi et al. |
| 7,708,737 | B2 | 5/2010 | Kraft et al. |
| 7,981,025 | B2 | 7/2011 | Pool |
| 7,988,357 | B2 | 8/2011 | Hornung et al. |
| 8,057,472 | B2 | 11/2011 | Walker |
| 8,197,490 | B2 | 6/2012 | Pool |
| 2006/0264944 | A1* | 11/2006 | Cole .................... 606/62 |
| 2008/0269744 | A1* | 10/2008 | Kay et al. ............ 606/62 |
| 2010/0137863 | A1* | 6/2010 | Munro .................. 606/64 |
| 2011/0046746 | A1 | 2/2011 | Rabiner et al. |
| 2011/0178604 | A1 | 7/2011 | Porter |
| 2011/0230883 | A1* | 9/2011 | Zahrly et al. ........ 606/63 |
| 2012/0209265 | A1* | 8/2012 | Pool .................... 606/55 |

FOREIGN PATENT DOCUMENTS

| | | |
|---|---|---|
| RU | 2302218 | 7/2007 |
| WO | WO2008030201 | 3/2008 |

OTHER PUBLICATIONS

Antoci et al., Pin-Tract Infection During Limb Lengthening Using External Fixation, Am J Orthop 2008; 37(9): E150-154.

Bell et al., Transfemoral Amputations: The Effect of Residual Limb Length and Orientation on Gait Analysis Outcome Measures, J Bone Joint Surg Am, 2013; 95: 408-414.

Brewster et al., Lower Limb Lengthening: Is There a Difference in the Lengthening Index and Infection Rates of Lengthening with External Fixators, External Fixators with Intramedullary nails or Intramedullary Nailing Alone: A Systematic Review of the Literature Eur J Orthop Surg Traumatol (2010) 20:103-108.

Cole et al., The Intramedullary Skeletal Kinetic Distractor (ISKD): First Clinical Results of a New Intramedullary Nail for Lengthening of the Femur and Tibia, Injury, Int. J. Care Injured 32 (2001) S-D-129-S-D-139.

Ilizarov, Clinical Application of the Tension-Stress Effect for Limb Lengthening, Clinical Orthopaedics and Related Resarch, Jan. 1990, No. 250, pp. 8-26.

Ilizarov, The Tension-Stress Effect on the Genesis and Growth of Tissues: Part 1. The influence of Stability of Fixation and Soft-Tissue Preservation, Clinical Orthopaedics and Related Research, Jan. 1989, No. 238, pp. 249-281.

Kenawey et al., Insufficient Bone Regenerate after Intramedullary Femoral Lengthening, Clin Orthop Relat Res (2011) 469:264-273.

Kocaoglu et al., Complications Encountered During Lengthening Over an Intramedullary Nail, The Journal of Bone and Joint Surgery, Incorporated, vol. 86-A, No. 11, Nov. 2004, pp. 2406-2411.

Mahboubian et al., Femoral Lengthening with Lengthening over a Nail has Fewer Complications than Intramedullary Skeletal Kinetic Distraction, Clin Orthop Relat Res (2012) 470:1221-1231.

Paley, Problems, Obstacles, and Complications of Limb Lengthening by the Ilizarov Technique, Clinical Orthopaedics and Related Research, Jan. 1990, No. 250, pp. 81-104.

Sakurakichi et al., The Relationship Between Distraction Length and Treatment Indices During Distraction Osteogenesis, J Orthop Sci (2002) 7:298-303.

Samchukov et al., Distraction Osteogenesis of the Orthopedic Skeleton: Basic Principles and Clinical Applications, Orthopedic Biology and Medicine: Musculoskeletal Tissue Regeneration, Biological Materials and Methods, pp. 183-198. 2008.

* cited by examiner

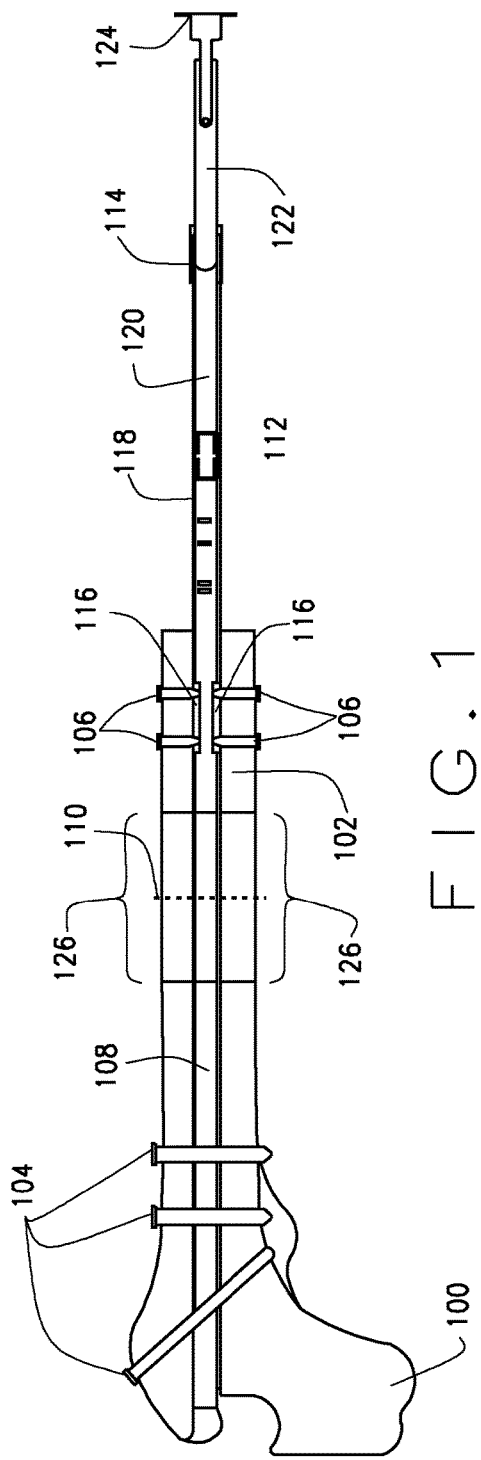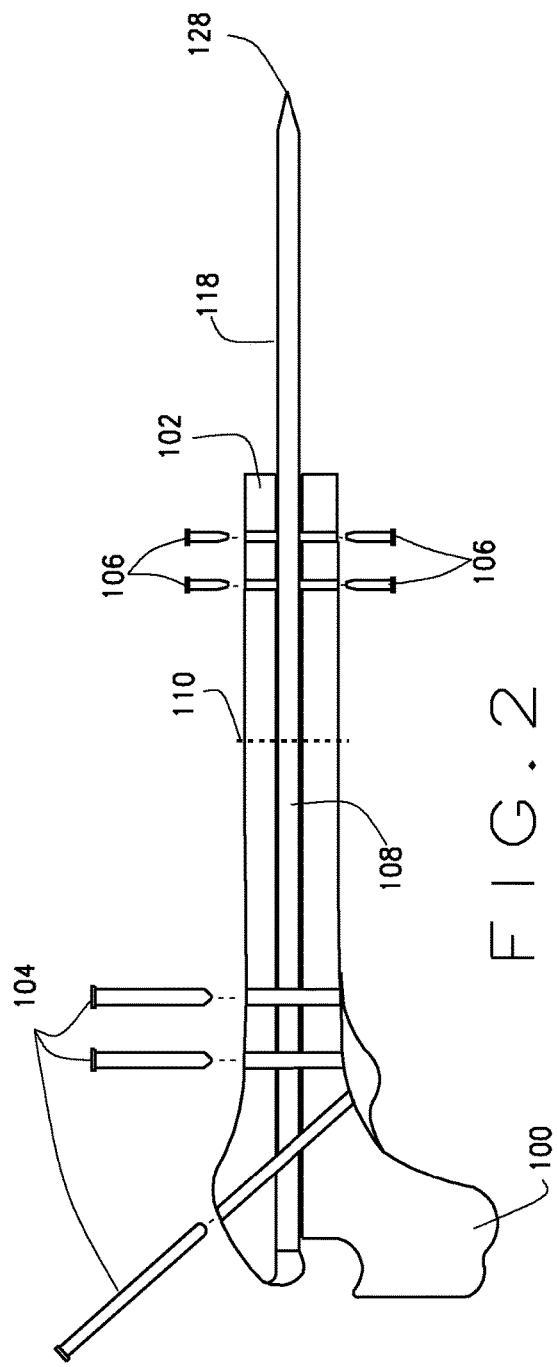

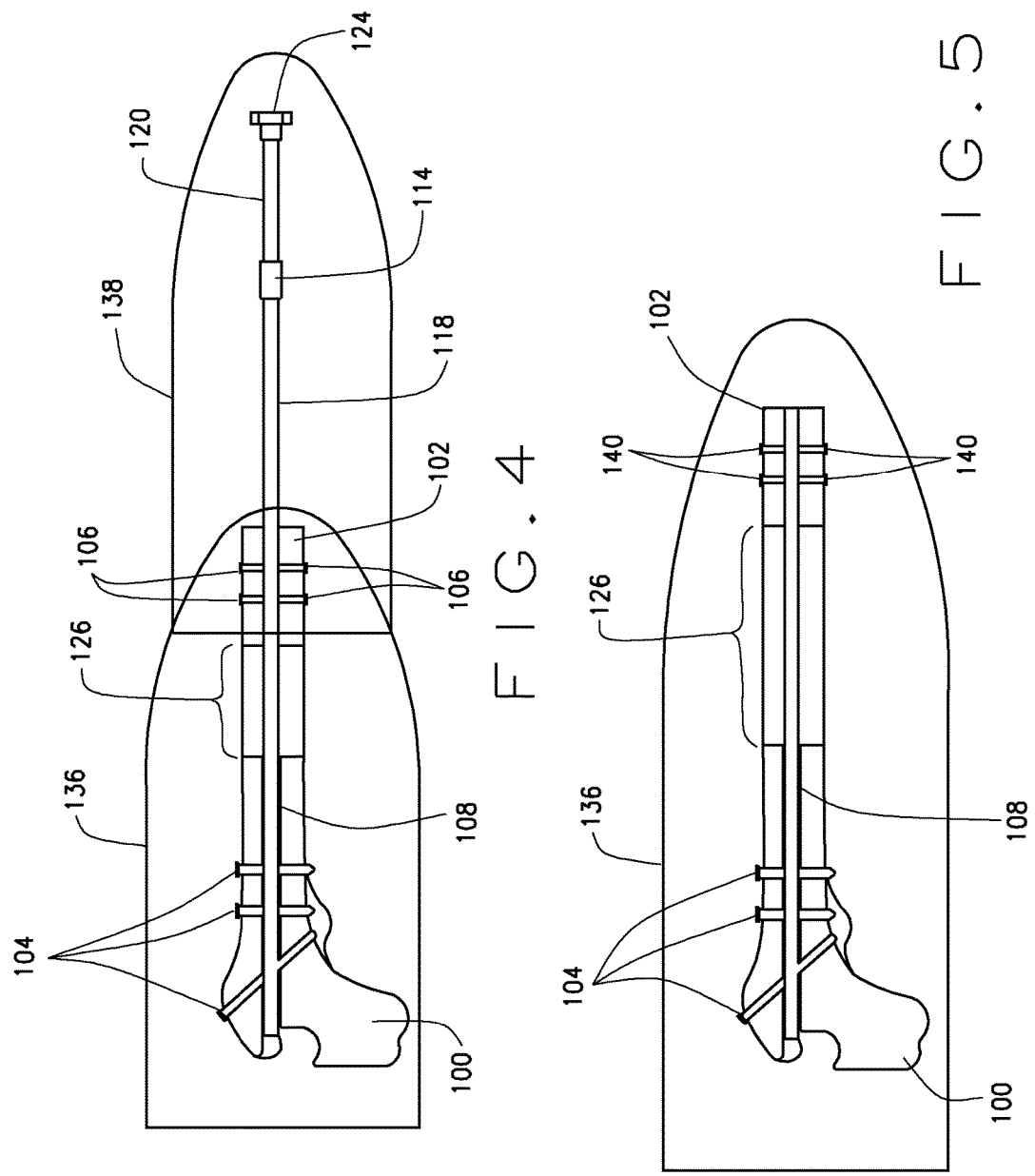

LIMB LENGTHENING SYSTEM FOR RESIDUAL LIMB

FIELD

The invention described herein relates to the field of limb lengthening through the use of a surgically implanted device.

BACKGROUND

Amputation of the arm or leg causes significant disability, the most effective treatment for which is replacement of the missing limb with a prosthetic device. However, amputations that result in short residual limbs pose significant problems for fitting and suspension of a prosthetic device, and control of the prosthesis is compromised because of the short length of the lever arm provided by the residual limb. This results in poor energy transfer between the limb and an attached prosthesis, as short lever arms generate less torque for a given force. This functional deficit is compounded when the lever arm is encased in very compliant tissue, such as a residual femur that is surrounded by the soft tissues of the thigh, which further impairs prosthesis control. Individuals with short residual limbs following leg amputation display greater gait asymmetries and gait changes than those with longer residual limbs (Bell et al. 2013). In addition, short residual legs reduce stability and balance when sitting and when performing transfers, such as getting on and off the toilet or into a car. Postural changes and compensatory mechanisms associated with use of short residual limbs can cause discomfort and injury to the spine or other body structures.

Lengthening of a limb can be accomplished through Distraction Osteogenesis (DO), a process that starts by performing an osteotomy; a surgical procedure wherein a bone is cut into two segments, a proximal segment (nearer to the body) and a distal segment (further from the body). The two segments are then gradually separated by an applied traction force at an expansion rate such as 1 mm per day (Ilizarov 1990). After the bone has been cut, new bone starts to form in the resulting gap as a result of natural bone fracture-healing mechanisms. The period when new bone is forming is known as the distraction phase. When the desired length is reached, the distraction force is discontinued and the new bone ossifies and remodels into mature bone during the consolidation phase (Samchukov 2008).

Current limb lengthening procedures that use DO rely on external devices (Ilizarov 1989) or fixators, which must be worn a minimum of 1 day for distraction and 2 days for consolidation for every millimeter of length gained, for a total of at least 3 days per millimeter of additional length. For example, to gain 75 mm of length, the patient would have to wear such a device for at least 225 days, or 7.5 months. Frequently, complications extend this timeline, such that it can sometimes be almost twice as long (Sakurakichi et al. 2002). Additionally, some external components of these devices must pass through the skin and attach to the bone at a minimum of 4 places, creating 4-8 percutaneous wounds that pose a considerable risk of infection. Thus an additional complication associated with use of these devices is infection and scarring at sites of skin penetration. Such complications are reported in up to 59% of patients (Paley 1990). Some studies show skin infection rates as high as 78-100% (Antoci et al. 2008). Infection rates decrease with fewer points of skin penetration (Brewster et al. 2010).

Because of their design, traditional external fixator DO devices are large and cumbersome. They interfere with the ability to wear clothing and to move around in bed, which affects sleep. The Ilizarov technique requires a cage that encircles the limb so that the patient must keep their limb in an abducted position, which is uncomfortable, reduces mobility, interferes with the use of crutches or wheelchairs, and impairs general function. External fixators, which are placed on the lateral side of the leg, also interfere with the use of crutches, use of a wheelchair, and general function.

The prior art devices preclude an active lifestyle for several months, which may contribute to physical decline, depression, and other psychological consequences. Despite the advantages provided by a longer residual limb, the inordinate burden imposed on the patient by these devices and the relatively high rates of complication often limit the use of DO to lengthen residual limbs in amputees. Utilization of the prior art is often too difficult, physically and emotionally, for a patient with an amputation.

Lengthening-over-a-nail (LON) is a technique for patients with intact limbs that decreases the time a patient needs to wear the external fixator device. During the distraction phase, the LON approach utilizes both an external fixator and an internal nail inserted into the medulla of the bone, known as an intramedullary nail or IM nail. The external device is removed during the consolidation phase; however, the IM nail remains in the bone to provide support. By decreasing the required wear time of the external fixator device, LON techniques have led to decreased rates of superficial infection from 36.2% with traditional external fixator devices to 1.4% with LON (Brewster et al. 2010). Thus, limiting the time that external, percutaneous components are required can decrease overall complications in addition to improving patient comfort and quality of life (Kocaoglu et al. 2004; Mahboubian et al. 2012).

Several intramedullary devices for DO exist for patients (usually children) with intact limbs. The Intramedullary Skeletal Kinetic Distractor (ISKD) (Cole et al. 2001) (Orthofix Inc., Texas) is the only FDA-approved intramedullary DO device available in the United States at this time. These devices allow bone lengthening in patients with intact limbs, without the need for any percutaneous devices. However, the ISKD has been shown to produce variable rates of distraction, which increases the risk of non-union, pseudoarthrosis, or early consolidation (Mahboubian et al. 2012). Reviews of this and other devices have proven that poorly controlled distraction (e.g., lengthening>1.5 mm/day, so-called runaway) is an important risk factor for poor bone formation (Kenawey et al. 2011).

SUMMARY

The present invention is directed towards an Intramedullary Distraction Osteotomy (IM DO) system, and corresponding methods, for lengthening a bone in the residual limb of upper or lower limb amputees.

The foregoing and other aspects of the present invention will become more apparent from the following detailed description of the invention when considered in conjunction with the accompanying drawings.

BRIEF DESCRIPTION OF THE DRAWINGS

FIG. 1 is a cross-sectional diagram of the IM DO apparatus showing placement within a residual bone.

FIG. 2 is a diagram of the IM DO apparatus showing anchor points of IM nail after insertion into a residual bone.

FIG. 4 is a diagram showing the padded covering of the distal limb and protruding IM DO apparatus during the distraction phase.

FIG. 5 shows the IM DO nail in situ during the consolidation phase, after removal of the percutaneous lead screw and other external components.

Corresponding reference characters indicate corresponding elements among the view of the drawings. The headings used in the figures should not be interpreted to limit the scope of the claims.

LIST OF NUMERALS IN DRAWINGS

Figure 3:
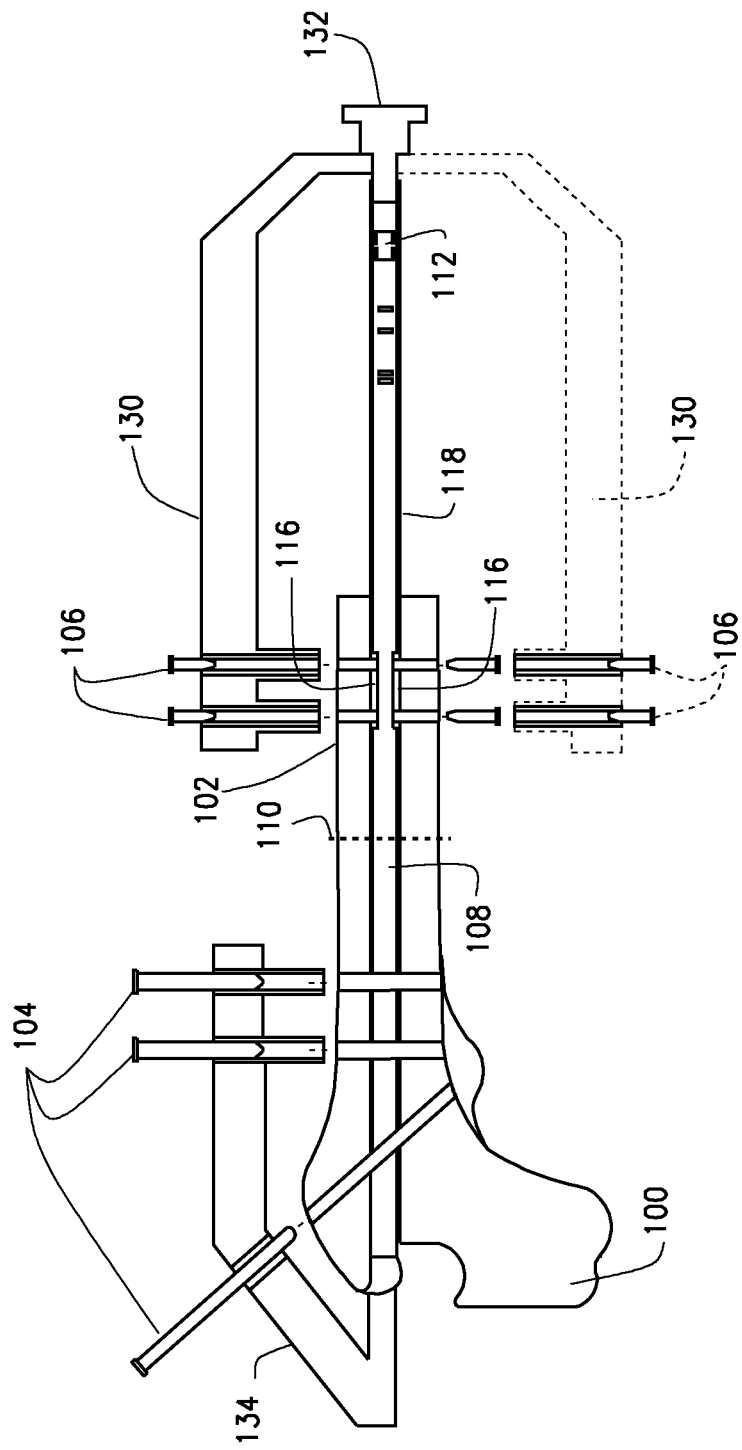
FIG. 3 is a diagram of the nail guide(s) for the correct placement for (i) the bicortical screws that anchor the IM nail to the proximal bone, and (ii) the unicortical screws that anchor the distal bone segment, extension tube, and anti-rotation lock.

| | |
|---|---|
| 100 | Proximal bone segment |
| 102 | Distal bone segment |
| 104 | Bicortical screws |
| 106 | Unicortical, screws |
| 108 | Intramedullary (IM) nail |
| 110 | Bone division site |
| 112 | Sealing plug |
| 114 | Friction nut assembly |
| 116 | Anti-rotation lock |
| 118 | Extension tube |
| 120 | Lead screw |
| 122 | Additional lead screw segment(s) |
| 124 | Lengthening knob |
| 126 | New bone |
| 128 | Pointed end cap |
| 130 | Distal nail guide |
| 132 | Nail guide end cap |
| 134 | Proximal nail guide |
| 136 | Residual limb |
| 138 | Padding |
| 140 | Bicortical screws |

DETAILED DESCRIPTION

Referring to the drawings, embodiments of the device are illustrated and indicated numerically in FIGS. 1-5. The image of a human femur is used as an example in the drawings, although embodiments described herein could be used on a variety of upper limb and lower limb bones including, but not restricted to, the femur, tibia, fibula, humerus, radius, and ulna.

FIG. 1 shows one embodiment of the invention installed in the residual bone of an amputated limb. The residual bone is cut (i.e., an osteotomy is performed) in an appropriate location (e.g., at position shown by dotted line 110) to obtain two separable bone segments: a proximal bone segment 100 and a distal bone segment 102. An IM nail 108 and extension tube 118 are inserted through the intramedullary canal, and are shown passing through the proximal bone segment 100, new bone 126 forming after surgery and during the lengthening procedure, and the distal bone segment 102.

The distal ends of the extension tube 118 and IM nail 108 exit at the distal end of the residual bone and protrude from a single percutaneous (e.g. through-skin) opening at the distal end of the limb. Locating the single percutaneous component at the distal end of the residual limb allows the patient to more easily wear normal clothes. The device shown at FIG. 1 allows the patient to move in bed and use a wheelchair or crutches, improving the patient's sleep and mobility. Additionally, having only one percutaneous opening, as disclosed in FIG. 1, reduces infection risk.

Bicortical screws 104 secure the IM nail 108 to the proximal bone segment 100. The IM nail 108 has two grooves that run longitudinally on the outside of the nail, proximal to distal, from bicortical screws 104 to the distal end of the IM nail 108, on opposite sides (such as the top and bottom) of IM nail 108. Anti-rotation lock 116 comprises anti-rotation keys that fit into these grooves. The anti-rotation lock 116 is secured to the extension tube 118 by unicortical screws 106. In this way, the anti-rotation lock 116 is operatively coupled to each of the IM nail 108 and the extension tube 118. However, it should be apparent to one of ordinary skill in the art that other manners of operatively coupling the anti-rotation lock 116 to the IM nail 108 and the extension tube 118 could be used. Anti-rotation lock 116 may be made of metal such as steel or titanium. Unicortical screws 106 pass through each side (e.g., top and bottom) of the distal bone segment 102, through specific holes in the extension tube 118, and then thread into the anti-rotation lock 116. This anchors said distal bone segment 102 to the extension tube 118. Once secured, the keys in anti-rotation lock 116 ride in the linear grooves of the IM nail 108 and prevent relative rotation between proximal bone segment 100 and distal bone segment 102.

The extension tube 118 may include a microbial barrier system. In one embodiment, the microbial barrier system includes a sealing plug 112 that is inserted into extension tube 118 prior to surgery to prevent entry of microbial contaminants. In one embodiment this sealing plug 112 comprises a short cylinder with two or more O-rings that fit into shallow grooves in extension tube 118 around the circumference of the plug. When the O-rings are inserted into the extension tube 118, they form a tight seal with the extension tube 118 which prevents infectious agents from entering the extension tube 118. In other embodiments of the microbial barrier system, the distal part of extension tube 118, between the sealing plug 112 and the friction nut 114, may be filled with gel or other substance containing antimicrobial agents, such as iodinated petroleum jelly.

The extension tube 118 has metal (such as steel or titanium) threading at its distal end. After surgical insertion of the extension tube 118, a friction nut assembly 114 is screwed onto this threading on extension tube 118. A lead screw 120 is threaded through the friction nut assembly 114 and metal threading at the distal end of the extension tube 118 until the proximal end of lead screw 120 reaches the sealing plug 112. The friction nut assembly 114 applies friction to the lead screw 120 so that it is not easily or accidently turned and is tight enough to prevent most material from entering the distal end of the extension tube, thus keeping the distal end of the extension tube relatively clean.

The distal end of the lead screw 120 has internal threading, into which a lengthening knob 124 may be screwed. Lengthening knob 124 is used by the patient or another person to distract or lengthen the limb. In one embodiment, the mechanism regulating the expansion rate between the IM nail 108 and extension tube 118 comprises lengthening knob 124, which can be turned in stepwise fashion and at varying, but accurately controlled rates according to the clinical needs of the patient. The degree of bone lengthening can be accurately measured by markers on the extension tube 118 or by counting the number of turns of the lengthening knob 124. The lengthening knob 124 can be made to turn in only one direction to prevent the patient from inadvertently backing out the lead screw 120.

Lengthening knob 124 turns the lead screw 120, which in turn pushes on the sealing plug 112, which pushes on the IM nail 108. The IM nail 108, held in place by bicortical screws 104, does not move. As a result, the extension tube 118 is pulled distally by the lead screw 120 turning through the threads at the distal end of extension tube 118. The extension tube 118 is prevented from rotating by the keys in the anti-rotation locks 116 that fit into longitudinal grooves in the IM nail 108. As extension tube 118 slides over the IM nail 108, the distance between the proximal bone segment 100 and distal bone segment 102 is increased and new bone 126 forms within as a result of the body's natural healing mechanisms. In this embodiment, the lead screw 120 is operatively coupled to the IM nail 108 through the lead screw's application of force upon sealing plug 112. It should be apparent to one of ordinary skill in the art that other manners of operatively coupling the lead screw 120 to the IM nail 108, so as to allow for bone distraction, could be used.

If desired, additional lead screw segments 122 can be attached to the lead screw 120. Use of one or more additional lead screw segments 122 allows lead screw 120 to be shorter, limiting the distance that the IM DO device must initially protrude distally from the residual limb, while still allowing for substantial lengthening of said limb. In one embodiment, the lead screw 120 enables limb lengthening, until the distal end of the residual limb nears lengthening knob 124. Then the lengthening knob 124 may be removed and an additional lead screw segment 122 may be threaded onto the lead screw 120, effectively lengthening lead screw 120. The distal end of additional lead screw segment 122 includes threading or other means known in the art for attachment to another additional lead screw segment 122. Lead screw 120 and any additional lead screw segments 122 together make up the lengthening screw of the IM DO system. The lengthening knob 124 then may be re-mounted at the end of the additional lead screw segment 122, allowing limb lengthening to continue.

Embodiments of the invention allow for regulated expansion of the new bone 126. In one embodiment, markings on the lengthening knob 124 can be used to provide accurate measures of daily bone extension. Alternatively, the length of exposed lead screw 120 and any additional lead screw segments 122 can be measured to determine the total amount of bone/limb extension. The rate of expansion can be controlled by the frequency at which the lengthening knob 124 is turned and degree to which said knob 124 is turned. The rate of expansion can thus be determined and controlled for each individual patient.

FIG. 2 refers to a cross-section of one embodiment of the IM DO system showing the initial stages of an IM DO procedure. The IM nail 108 and extension tube 118 with the seal plug 112 can be inserted into the bone from either the proximal end or the distal end of the residual bone and can be inserted either before or after the osteotomy. In one embodiment, the surgeon drills an appropriately sized hole through the femoral neck, into the intramedullary canal, and through the canal to the end of the remaining femur. The osteotomy is then performed just distal to the trochanters, breaking the bone into two segments.

The IM nail 108, extension tube 118, anti-rotation lock 116, sealing plug 112 and pointed end cap 128 are kept in a sterile container until prior to the surgery, when they are assembled in a sterilized manner. The surgeon inserts the pointed end cap 128 into the proximal femur and pushes the sterile assembly all the way through the proximal bone segment, the distal bone segment, and finally out the end of the limb through a small percutaneous hole cut in the soft tissues. The pointed end cap 128 facilitates passage of the sterile assembly through the bone and soft tissue with minimal damage to said tissues and keeps material out of the sterile assembly. In addition, the pointed end cap 128 helps the surgeon to feel the end of the device in order to know where exactly to cut the small percutaneous hole.

Once the IM DO device is in place, a proximal nail guide 134 (see FIG. 3) is threaded into place in a threaded hole at the proximal end of the IM nail 108. This guide is used to place the bicortical screws 104. With the IM nail 108/ extension tube 118 assembly protruding from the end of the residual limb, the extension tube 118, sealing plug 112 and anti-rotation lock 116 are at their fully compressed position, with the holes in the extension tube 118 aligned with the keys in anti-rotation lock 116 and at the correct position within the distal bone segment 102. A distal nail guide 130, shown in FIG. 3, is attached to the distal end of the extension tube 118 to enable accurate placement of the unicortical screws 106. In one embodiment, the distal nail guide 130 is held in place by a nail guide end cap 132 which screws into the end of the extension tube 118. A notch on the nail end guide cap 132 prevents the distal nail guide 130 from rotating with respect to the extension tube 118. The surgeon then uses the distal nail guide 130 to surgically place the unicortical screws 106 through the cortex of the distal bone segment 102, through the holes in the extension tube 118 and into the anti-rotation lock 116. After the unicortical screws 106 have been placed on one side of the distal bone segment 102, the nail guide end cap 132 can be removed and the distal nail guide 130 may be rotated 180 degrees about the extension tube 118. The dotted outline in FIG. 3 shows the distal nail guide 130 in fully-rotated position. The nail guide end cap 132 is then screwed back into the end of the extension tube 118, and the notch serving to hold the nail guide 118 in place is rotated 180 degrees from its previous position in order to prevent rotational movement, as previously described. In an alternative embodiment, a second distal nail guide, rotated 180 degrees from the first distal nail guide 130 so that the second distal nail guide is positioned according to the dotted outline in FIG. 3, may be used instead of a rotating nail guide.

The distal bone segment 102 is anchored by unicortical screws 106 (or other appropriate anchoring) to the proximal end of the extension tube 118 using the distal nail guide 130. Once placement has been determined, distal nail guide 130 is removed. Unicortical screws 106 pass through the bone cortex on opposite sides (e.g., top and bottom as shown in FIG. 2) and through holes in the extension tube 118 and then thread into anti-rotation lock 116 located within the proximal end of the extension tube 118. The distal bone segment 102 is thus anchored to the extension tube 118 by unicortical screws 106. The anti-rotation lock 116 prevents rotation of the extension tube 118 with respect to the IM nail 108. From one to four distal unicortical screws can be used. Bicortical screws 104 could be inserted into proximal bone segment 100, as shown in FIG. 3, from the lateral side of the limb or otherwise as known in the art.

After bone segments 100 and 102 are secured and distal nail guide 130 is removed, the friction nut assembly 114 (see FIG. 1) is threaded onto the end of the extension tube 118 and locked in place. In one embodiment, friction nut assembly 114 comprises a friction nut, with a set screw running through the side of the friction nut for locking. The lead screw 120 is then threaded through the friction nut assembly 114 and extension tube threading until it firmly presses the sealing plug 112 against the IM nail 108. The lengthening knob 124 is then mounted on the distal end of the lead screw 120.

In one embodiment, the lead screw 120 in the distal end of the extension tube 118 may be screwed in or out by a lengthening knob 124. As described above, turning the lengthening knob 124 moves the extension tube 118 in a distal direction while lead screw 120 pushes against the sealing plug 112 and IM nail 108, which is anchored to the proximal bone segment 100, thus placing tension on the distal bone segment 102 and pulling it away from the proximal bone segment 100. This process progressively generates a gap between bone segments that becomes filled with new bone 126. The IM nail 108 stabilizes said new bone 126 and, in combination with the anti-rotating lock 116, maintains correct alignment of the proximal (100) and distal (102) segments of the residual bone. In another embodiment, the turning knob 124 only allows turning in one direction, so that the patient cannot accidentally turn the lead screw 120 backwards.

FIG. 4 shows the system in place within the residual limb 136. After wound care and extension adjustment, a padding 138 is placed over the protruding components of the system to prevent the external component of the IM DO system from causing irritation of injury to the patient's other limb or body, to provide a more normal limb diameter for patient comfort, and to shield the IM DO system from sudden impact or other damage. The padding 138 is readily removable to allow access to the lengthening knob 124 and percutaneous wound. The padding 138 may also extend over the distal limb. Padding 138 may be made from foam or another suitable material.

FIG. 5 shows the IM nail 108 contained entirely within the residual limb 136 during the consolidation phase. The length of the IM nail 108, lead screw 120, and additional screw segments 122 is such that the distal end of the IM nail 108 will be coincident with the distal end of the distal bone segment 102 when the final desired length has been achieved. Once the residual bone has reached the final desired length, certain components may be removed. The lead screw 120 and any additional lead screw segments 122, the extension tube 118, and sealing plug 112 can be removed by removing the unicortical screws 106 and pulling the extension tube 118, with its contents, distally out of the end of the limb. After removal of the extension tube 118, the distal bone segment 102 is re-anchored to the distal end of the IM nail 108 using bicortical screws 140. The distal nail guide 130 can be used if desired. The distal wound may be closed by the surgeon. The new bone 126, which formed in the gap generated by the expansion procedure, is allowed to remodel and ossify into mature bone, with the continuing additional support of the IM nail 108. The IM nail 108 remains in place to provide structural support to the bone during the consolidation phase and may provide sufficient strength to allow the treated limb to begin weight-bearing activities earlier in the consolidation phase. In this manner, there are no percutaneous devices protruding through the patient's skin during the long consolidation phase. When the consolidation phase is complete and the patient has a longer limb with a mature bone, the IM nail and any remaining components can be surgically removed, if desired.

The embodiments described herein provide several advantages for lengthening an amputated limb. Such advantages, in addition to those already described, include: limited damage to a patient's soft tissue, limited points of skin penetration, more accurate control of lengthening, adequate stabilization of the limb during the consolidation phase, and sufficient increase in limb length to allow for improved prosthetic fitting and function. Removal of the IM DO components after the lengthening phase of treatment allows healing of the percutaneous wound, which further reduces infection risk. Positioning the lead screw 120 at the distal end of the residual limb improves the overall comfort of the user and reduces interference with daily life activities such as wearing clothing, mobility, and sleep. In addition, no external or percutaneous device is required during the consolidation phase, thus further reducing effects on daily life activities. The IM nail 108 supports the residual bone during the lengthening (distraction) and consolidation phases and may allow earlier return to use of the residual limb for weight bearing activities and prosthesis use. It should be understood that any advantage described herein is not intended to limit the scope of the invention.

The invention claimed is:

1. An apparatus for increasing bone length, comprising:
   a. an intramedullary nail that is configured to be coupled to a proximal bone section;
   b. an extension tube comprising a proximal portion configured to be coupled to a distal bone section and a distal portion configured to extend through a skin opening distal to the distal bone section during a distraction phase of the bone the distal portion of the extension tube defining a distal end, the extension tube further defining an opening at the distal end of the distal portion; and
   c. a lengthening screw that is configured to be coupled to each of the intramedullary nail and the distal portion of the extension tube and to pass through the opening at the distal end of the distal portion, wherein the lengthening screw is configured to move the extension tube distally from the intramedullary nail in response to an external force.

2. The apparatus of claim 1, further comprising an anti-rotation lock that is configured to be coupled to each of the intramedullary nail and the extension tube, wherein the anti-rotation lock is configured to prevent rotation of the extension tube relative to the intramedullary nail.

3. The apparatus of claim 2, wherein the anti-rotation lock comprises keys that are configured to be coupled to grooves defined on the intramedullary nail.

4. The apparatus of claim 2, further comprising one or more lead screw segments for attachment between the extension tube and a lengthening knob.

5. The apparatus of claim 4, further comprising a mechanism for regulating the expansion rate between the intramedullary nail and the extension tube.

6. The apparatus of claim 5, further comprising a microbial barrier system for reducing infection.

7. The apparatus of claim 6, further comprising one or more nail guides for anchoring the apparatus to bone.

8. The apparatus of claim 7, wherein the apparatus is packaged in a sterilized kit.

9. The apparatus of claim 1, further comprising one or more lead screw segments for attachment between the extension tube and a lengthening knob.

10. The apparatus of claim 1, further comprising a rotatable knob for regulating the expansion rate between the intramedullary nail and the extension tube.

11. The apparatus of claim 10, wherein the rotatable knob is attached to a distal end of the lengthening screw that extends through the skin opening.

12. The apparatus of claim 10, further comprising a lead screw segment attached to a distal end of the lengthening screw, wherein the rotatable knob is attached to a distal end of the lead screw segment that extends through the skin opening.

13. The apparatus of claim 1, further comprising an antimicrobial substance disposed so as to fill a cross-sectional portion of the extension tube.

14. The apparatus of claim 1, further comprising one or more nail guides for anchoring the apparatus to bone.

15. The apparatus of claim 14, wherein at least one of the nail guides is a distal nail guide.

16. The apparatus of claim 15, further comprising a nail guide end cap for preventing the at least one distal nail guide from rotating with respect to the extension tube.

17. The apparatus of claim 1, wherein the apparatus is packaged in a sterilized kit.

18. The apparatus of claim 1, wherein the extension tube comprises a sealing plug within the proximal portion, for prevention of microbial contamination.

19. The apparatus of claim 18, wherein the lengthening screw is configured to transfer said external force through the sealing plug in order to move the extension tube distally from the intramedullary nail.

20. The apparatus of claim 12, further comprising an antimicrobial substance disposed so as to fill a cross-sectional portion of the extension tube distal to the sealing plug.

21. The apparatus of claim 1, further comprising a pointed end cap for facilitating passage of the apparatus through bone or soft tissue.

22. The apparatus of claim 1, further comprising a padding that is configured to cover a portion of the extension tube.

\* \* \* \* \*